(12) United States Patent
Karageozian

(10) Patent No.: US 7,141,610 B2
(45) Date of Patent: Nov. 28, 2006

(54) COMPOSITIONS AND METHODS FOR THE INDUCTION OF RETINAL DETACHMENTS

(75) Inventor: Hampar L. Karageozian, San Juan Capistrano, CA (US)

(73) Assignee: ISTA Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 10/160,135

(22) Filed: May 31, 2002

(65) Prior Publication Data

US 2003/0165486 A1 Sep. 4, 2003

Related U.S. Application Data

(63) Continuation of application No. PCT/US00/42455, filed on Dec. 1, 2000.

(60) Provisional application No. 60/168,830, filed on Dec. 3, 1999.

(51) Int. Cl.
*A01N 31/14* (2006.01)
*A61K 38/46* (2006.01)
*A61K 38/48* (2006.01)

(52) U.S. Cl. ................ 514/723; 424/94.62; 424/94.63; 424/94.67

(58) Field of Classification Search ............... 424/94.1, 424/94.6, 94.62
See application file for complete search history.

(56) References Cited

U.S. PATENT DOCUMENTS 5,866,120 A 2/1999 Karageozian et al.
6,060,463 A * 5/2000 Freeman ..................... 514/81

FOREIGN PATENT DOCUMENTS

WO WO 91 16070 10/1991
WO WO 99 21512 5/1999

OTHER PUBLICATIONS

Toews et al., "Turnover of Axonally Transported Phospholipids in Nerve Ending of Retinal Ganglion Cells", J. Neurochemistry 37(5): 1316-23 (1981).*
Reperant et al., "A Comparative Radioautographic Study of the Bidirectional Axonal and Trascellular Transport of Different Amino Acids and Sugars in the Lamprey Visual System", Brain Research 348 (2) : 348-54 (1985).*

* cited by examiner

*Primary Examiner*—Sandra E. Saucier
(74) *Attorney, Agent, or Firm*—Knobbe, Martens, Olson & Bear, LLP

(57) ABSTRACT

A method comprising administering by ocular route a dose of a glycol ether effective to induce retinal detachment.

10 Claims, 10 Drawing Sheets

COMPOSITIONS AND METHODS FOR THE INDUCTION OF RETINAL DETACHMENTS

CROSS-REFERENCE TO RELATED APPLICATIONS

This application is a continuation PCT Patent Application Serial Number PCTUS00/42455, filed on Dec. 1, 2000, and published in English, which claims priority to U.S. Provisional Application Ser. No. 60/168,830, filed Dec. 3, 1999, both of which are incorporated by reference.

FIELD OF THE INVENTION

The invention relates to compositions and methods for the non-surgical induction and treatment of retinal detachments. One embodiment relates to a pharmaceutical composition comprising a glycol ether effective for inducing and treating retinal detachments. Another embodiment relates to vision restoration achieved by surgically translocating retinal tissue. Yet another embodiment relates to the treatment of retinal detachments.

BACKGROUND OF THE INVENTION

Retinal detachment is generally regarded as a negative ophthalmic event to be avoided. Nevertheless, retinal detachment has recently been used as a method with which to treat retinal damaged, such as macular degeneration. In macular degeneration, photoreceptor cells that allow detailed vision degenerate in one focal area of the macula. The formation of this macular damage to photoreceptors results in a loss of sight in the afflicted subject.

One procedure to treat this disease is to surgically induce a retinal detachment. In one form of this procedure, a nick is surgically introduced into the retina of a subject. Subsequently a small amount of fluid is then introduced between the retina and the retinal space. The introduction of this fluid causes the separation of the retina from the retinal pigment epithelium. Once the retina is separated from its support layer it is then manually moved into a new position of the retina where photoreceptor cells are healthy and allow detailed vision, and is then reattached. Unfortunately, there are a number of complications with this procedure.

One complication resulting from the surgical detachment of the retina is that retinal pigment epithelia cells (RPE cells) are released into the vitreous humor. The introduction of these cells into the vitreous humor can lead to retinal damage by causing proliferative retinopathy and subretinal fibrosis.

Another complication arises during the manipulation of the detached retinal tissue as it is moved into a desired position. The retinal tissue is extremely fragile and surgical manipulations often will result in unintended tears in the retina. These tears reduce any therapeutic advantages that might result from the translocated retinal tissue.

In view of these limitations, what is needed is a non-surgical method of inducing retinal detachment.

SUMMARY OF THE INVENTION

The invention disclosed herein is directed to compositions and methods for inducing and treating retinal detachment. One embodiment of the invention relates to the use of a glycol ether in the manufacture of a medicament to induce retinal detachment. Another embodiment relates to the use of a glycol ether in the manufacture of a medicament to induce a non-surgical retinal translocation wherein the medicament is administered in a retinal detaching dose, wherein the detached retina is translocated from a first position to a second position, and the detached retinal tissue is then reattached. Another embodiment relates to the use of a glycol ether in the manufacture of a medicament to protect detached retinal tissue from degeneration. Another embodiment of the invention contemplates a method comprising administering by ocular route a dose of a glycol ether effective to induce retinal detachment. Another embodiment of the invention contemplates a method comprising the steps of administering by ocular route a dose of a glycol ether effective to induce retinal detachment; translocating a portion of retinal tissue from a first position to a second position; and reattaching said portion of retinal tissue.

BRIEF DESCRIPTION OF THE DRAWINGS

FIG. 2 illustrates two retinal detachments.

DETAILED DESCRIPTION OF THE INVENTION

Figure 1:
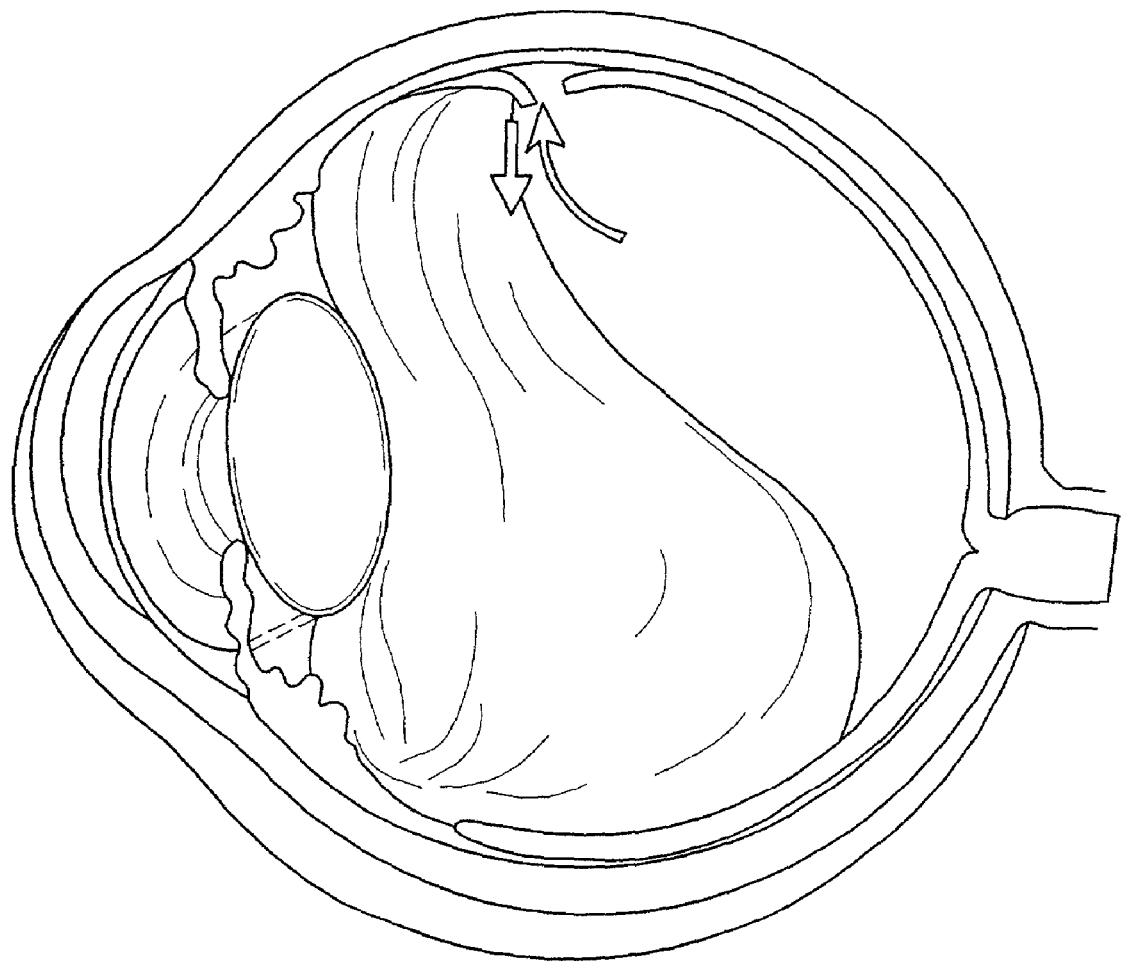
FIG. 1 shows a detached vitreous gel that has caused a retinal tear by exerting traction upon the retina at the site of vitreoretinal adhesion. The downward arrow indicates pressure exerted by the detached vitreous gel. The tissue immediately above the downward arrow shows a site of abnormal vitreoretinal adhesion. Immediately to the right of this site of abnormal vitreoretinal adhesion is a subretinal space. The upward facing arrow shows the direction of liquid passing into the subretinal space. The area below and to the right of the of subretinal space is liquid vitreous posterior to the vitreous gel. The vitreous gel is located immediately to the left of the liquid vitreous posterior to the vitreous gel.

The invention disclosed herein relates to compositions and methods for the induction of temporary retinal detachment in the eye of a subject mammal without retinal surgery. Additionally, treatment of retinal detachments is also provided below. To achieve these goals, typically a short-chain polymeric alcohol, preferably polyethylene glycol or another retinal detaching agent, is administered to the vitreal humor of a subject in need of retinal relocation therapy.

Retinal Adhesion

To better understand the problem to be solved, it will be helpful to understand the structure of the retina and the molecules and structures responsible for retinal adhesion. One important structure is the interphotoreceptor matrix (IPM). The IPM is not simply a sticky glue. It contains complex molecules, such as glycosaminoglycans, and has an elaborate structure in which domains of distinct chemical characteristics surround the rods and cones. These can be demonstrated by staining the matrix material with fluorescent binding molecules. The matrix serves several functions, which include physical support of the photoreceptors, transfer of nutrients and visual pigments, and the formation of an adhesive bond between neural retinal and RPE. These functions are largely controlled by the RPE, not only through synthesis of matrix materials and transport proteins, but also acutely through the transport of ions and water. The degree to which the IPM is hydrated or dehydrated alters its bonding properties and viscosity.

Retinal adhesion is a complex process, involving several complementary and interactive mechanisms. The neural retina is pressed in place by the vitreous gel, intraocular fluid pressure, and RPE water transport, which drive water through the semi permeable tissue. Also, some physical resistance prevents separation of the outer segments from the enveloping RPE microvilli. However, the strongest mechanism for the bonding of the retina to RPE space appears to be the IPM. When the neural retina is freshly peeled from the RPE, the IPM material stretches dramatically before it breaks, which shows that it is firmly attached to both neural retinal and RPE surfaces. It also is important to recognize that, despite these physical forces of adhesion, the strength of neural retinal adhesion is constantly and acutely dependent upon vital metabolism. [2]For example, neural retinal adhesive force drops to near zero within minutes after death and adhesive strength can be reversibly restored or enhanced by tissue oxygenation. The likely basis of these metabolic effects is water transport across the RPE, which controls the hydration and local ionic environment in the subneural retinal space and thereby the boding properties of the IPM material.

Neural retinas do not detach easily, which is perhaps a reflection of these multiple mechanisms for keeping it in place. However, detachment is more frequent in older eyes (which may be metabolically less competent); serious neural retinal detachments often are associated with local ischemic conditions, such as eclampsia and severe hypertension. When neural retinas have been detached experimentally and then allowed to reattach, full adhesive strength is not regained for more than 1 month. [3]Resynthesis of matrix domains after enzymatic destruction requires about 2 weeks and additional time may be needed for the RPE and photoreceptors to regain full microvillous intercalation. The clinical message is that neural retinal attachment is a complex and metabolically vital process, which is relevant to the pathophysiology of both neural retinal detachment, and the process of repair.

[4]Retinal attachment usually is maintained by: an adhesive-like mucopolysaccharide in the subretinal space; entotic pressure differences between the choroid and subretinal space; hydrostatic or hydraulic forces related to intraocular pressure; and metabolic transfer of ions and fluid by the retinal pigment epithelium (RPE).

Retinal detachment occurs when the combination of factors that promote retinal detachment overwhelms the normal attachment forces.

Rhegmatogenous retinal detachments are an important potential cause of reduced visual acuity, particularly in the subgroup of individuals who are predisposed to the development of retinal tears. Nearly all symptomatic rhegmatogenous retinal detachments progress to total blindness unless they are repaired successfully. Timely recognition of the symptoms and signs of retinal detachment is important to maximize the chances of a favorable surgical outcome and preserve visual acuity.

Epidemiology and Pathogenesis[4]

The essential requirements for a rhegmatogenous retinal detachment include a neural retinal break (rhegina=rent or rupture) and vitreous liquefaction sufficient to allow vitreous fluid to pass through the break into the subretinal space. The usual pathologic sequence that results in retinal detachment is vitreous liquefaction followed by a posterior vitreous detachment (PVD), which in turn causes a retinal tear at the site of a significant vitreoretinal adhesion (FIG. 1). All ocular conditions that are associated with an increased prevalence of vitreous liquefaction and PVD or with an increased number or extent of vitreoretinal adhesion are associated with a high incidence of retinal detachment.

Factors That Cause Retinal Detachment

The major factors associated with the development of retinal detachment include retinal breaks, vitreous liquefaction and detachment, traction on the retina (vitreoretinal traction), and intraocular fluid currents associated with movement of liquid vitreous and subretinal fluid. The majority of eyes with retinal breaks do not develop retinal detachment because the physiologic forces present are sufficient to hold the retina in place.

Retinal Breaks

Retinal breaks traditionally are classified as holes, tears or dialyses. Retinal holes are fall-thickness retinal defects that are not associated with persistent vitreoretinal traction in their vicinity. They occur usually as a result of localized atrophic intraretinal abnormalities.

Figure 2B:
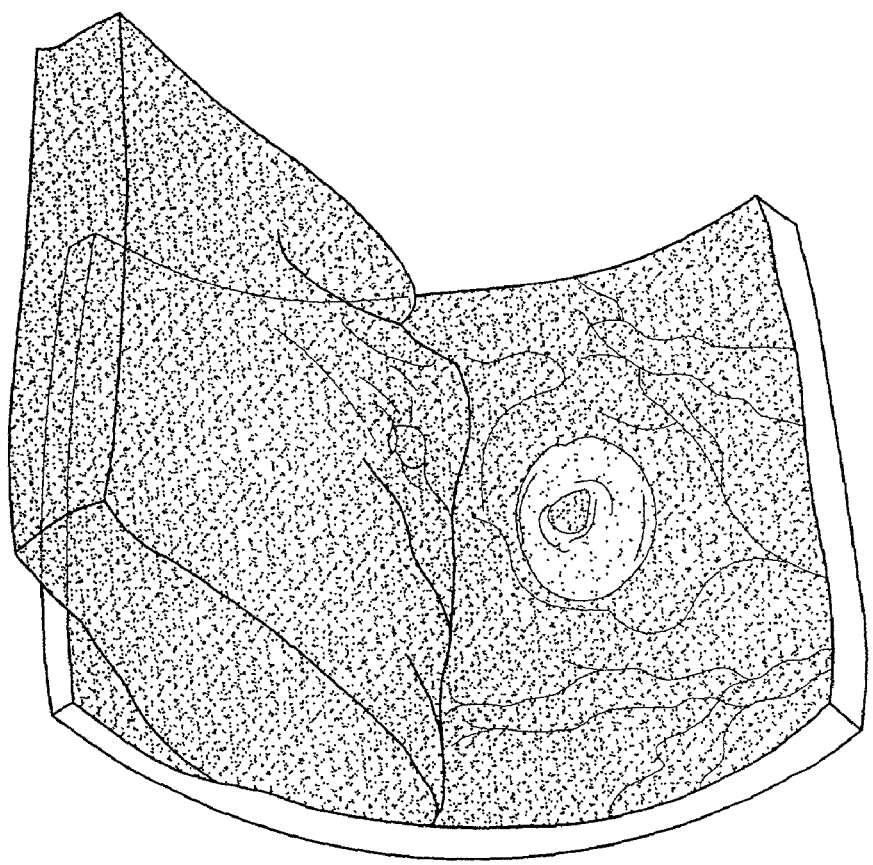
FIG. 2b also shows a retinal tear, however, in this figure, retinal integrity is lost due to the formation of a retinal hole that is shown on the retina itself. A free operculum is shown above the retinal hole on the vitreous gel that protrudes from the retina.
Figure 2A:
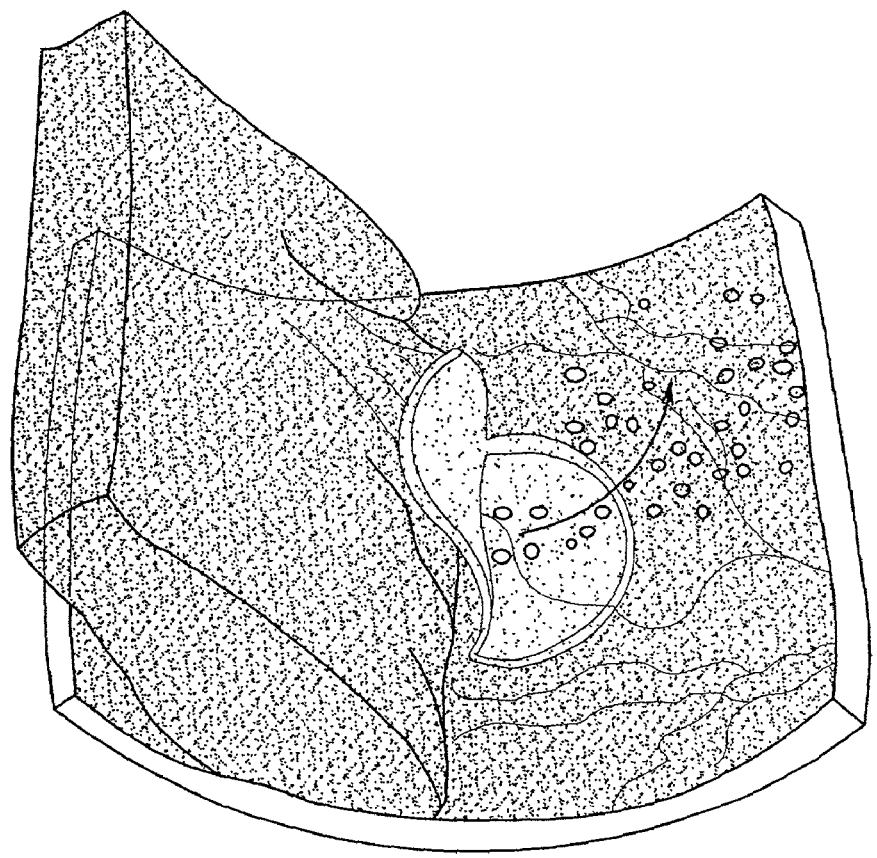
FIG. 2a shows a cross-section of an eye where the curved structure is the retina and the rectangular structure protruding to the right represents the vitreous gel. In the center of this figure is presented a retinal tear. An anterior flap is indicated by the flap of tissue extended out of the plane of the figure. The arrow indicates the outflow of retinal components resulting from the loss of integrity of the retina at the site of the tear.

Retinal tears usually are produced by PVD and subsequent vitreoretinal traction at the site of a significant vitreoretinal adhesion (FIG. 1 and FIG. 2). Vitreous traction usually persists at the edge of a tear, which promotes progression of the retinal detachment.

Dialyses are linear retinal breaks that occur along the ora serrata. While most are strongly associated with blunt ocular trauma, dialyses can occur spontaneously in certain individuals.

Vitreous Liquefaction and Detachment

Aging of the human vitreous (synchysis senilis) is characterized by liquefaction of the vitreous gel and the occurrence of progressively enlarging pools of fluid (lacunae) within the gel. These optically empty liquid spaces continue to coalesce as age advances; extensive liquefaction within the vitreous cavity leads to a reduction in both the shock-absorbing capabilities and the stability of the gel. Accelerated vitreous liquefaction is associated with significant myopia, surgical and nonsurgical trauma, intraocular inflammation, and a variety of other congenital, inherited, or acquired ocular disorders.

Figure 3:
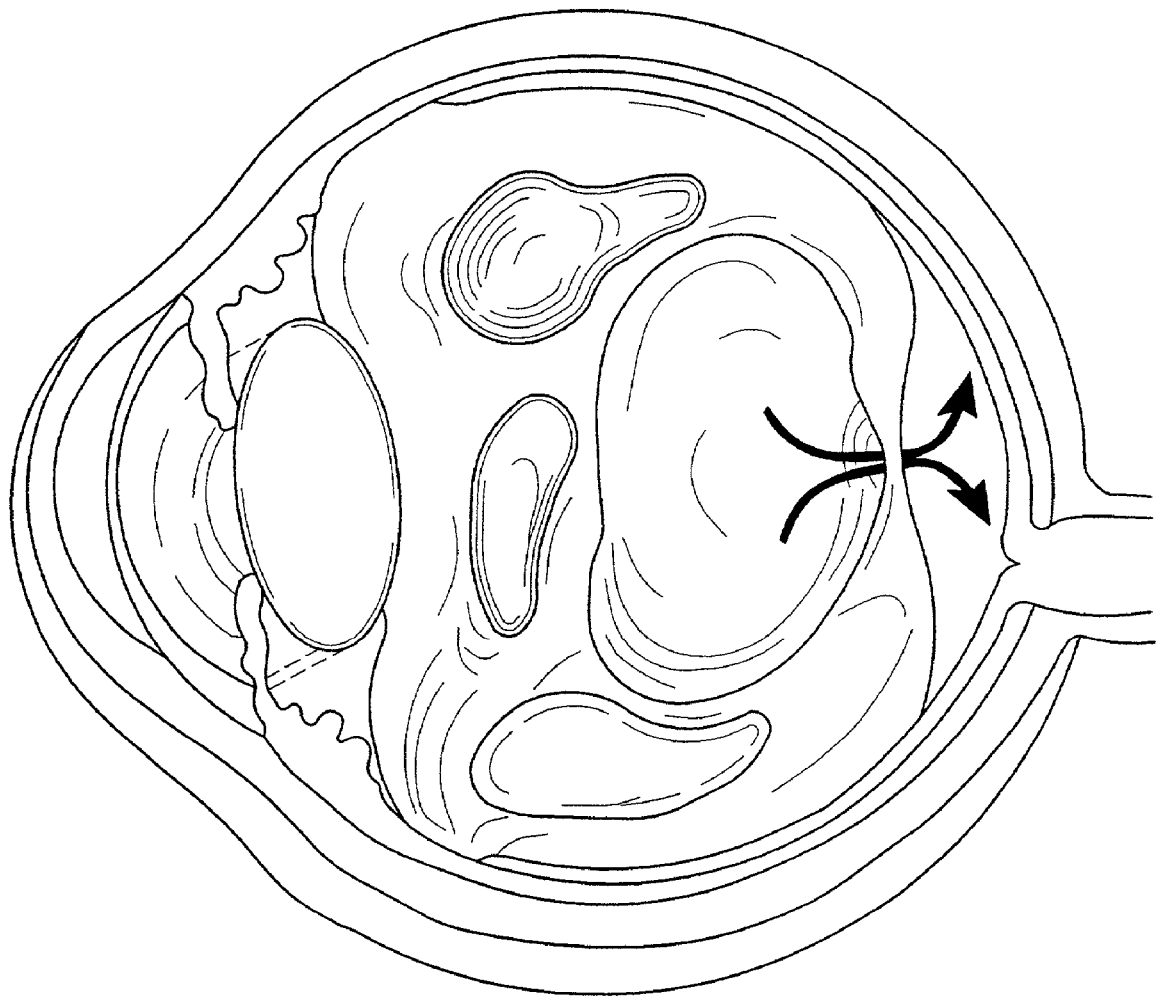
FIG. 3 graphically illustrates the condition of posterior vitreal detachment. This figure shows a fluid filled central lacuna in the vitreous humor of an eye. The arrows show fluid flow from the central lacuna into a posterior vitreous surface separated from the retina.
Figure 4:
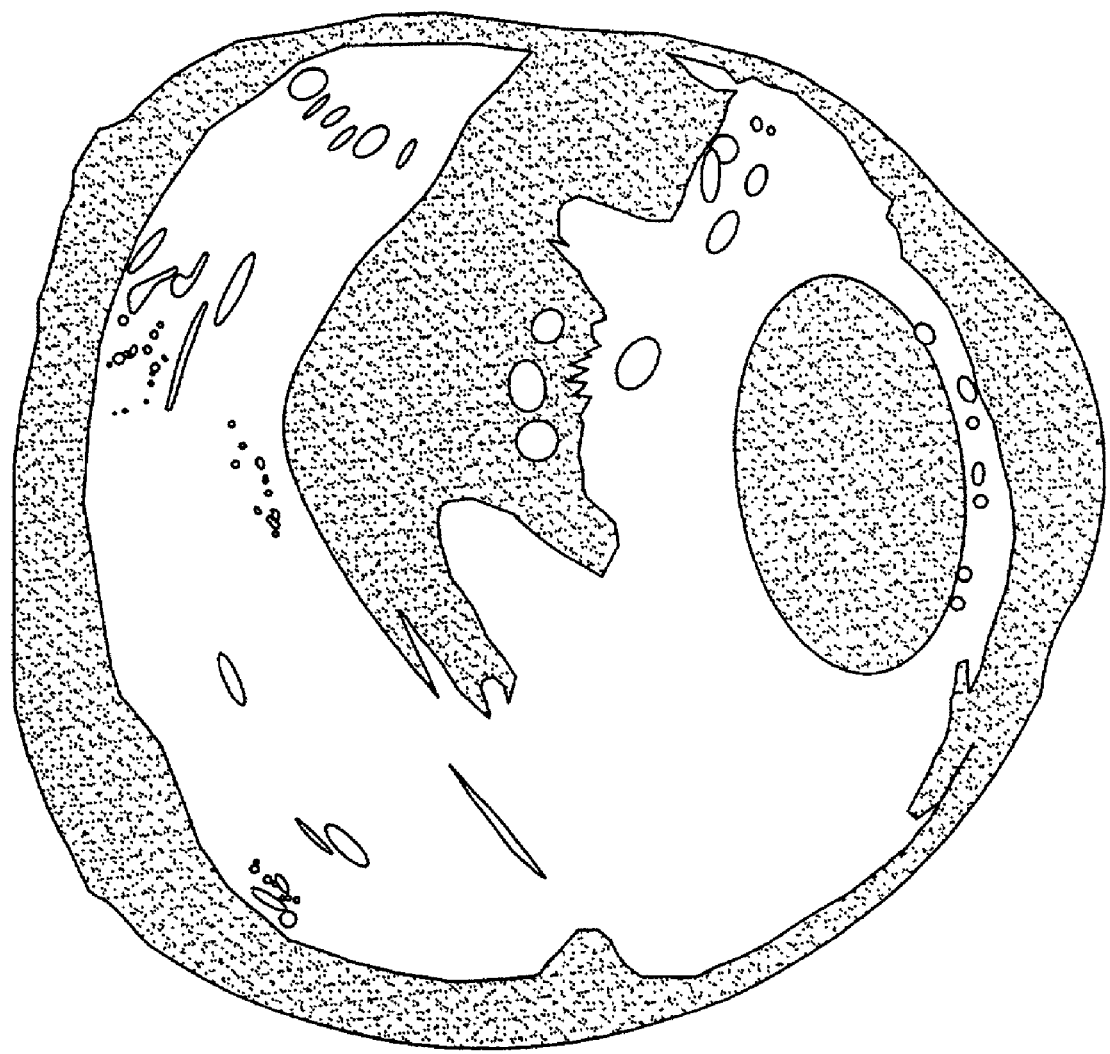
FIG. 4 is a photograph of a bisected globe in which the cortical vitreous has partially separated from the retina.

Posterior vitreous detachment, routinely termed PVD or posterior vitreous detachment, usually occurs as an acute event after significant liquefaction of the vitreous gel. The precipitating event probably is a break in the posterior cortical vitreous in the region of the macula. [5]This is followed by the immediate passage of intravitreal fluid into the space between the cortical vitreous and retina (FIG. 3). Characteristically, this rapid movement of fluid and the associated collapse of the remaining structure of the gel result in extensive separation of the vitreous gel and retina posterior to the vitreous base, especially in the superior quadrants. Partial PVDs usually progress rapidly (within days) to become complete (FIG. 4).

Traction on the Retina

Figure 5:
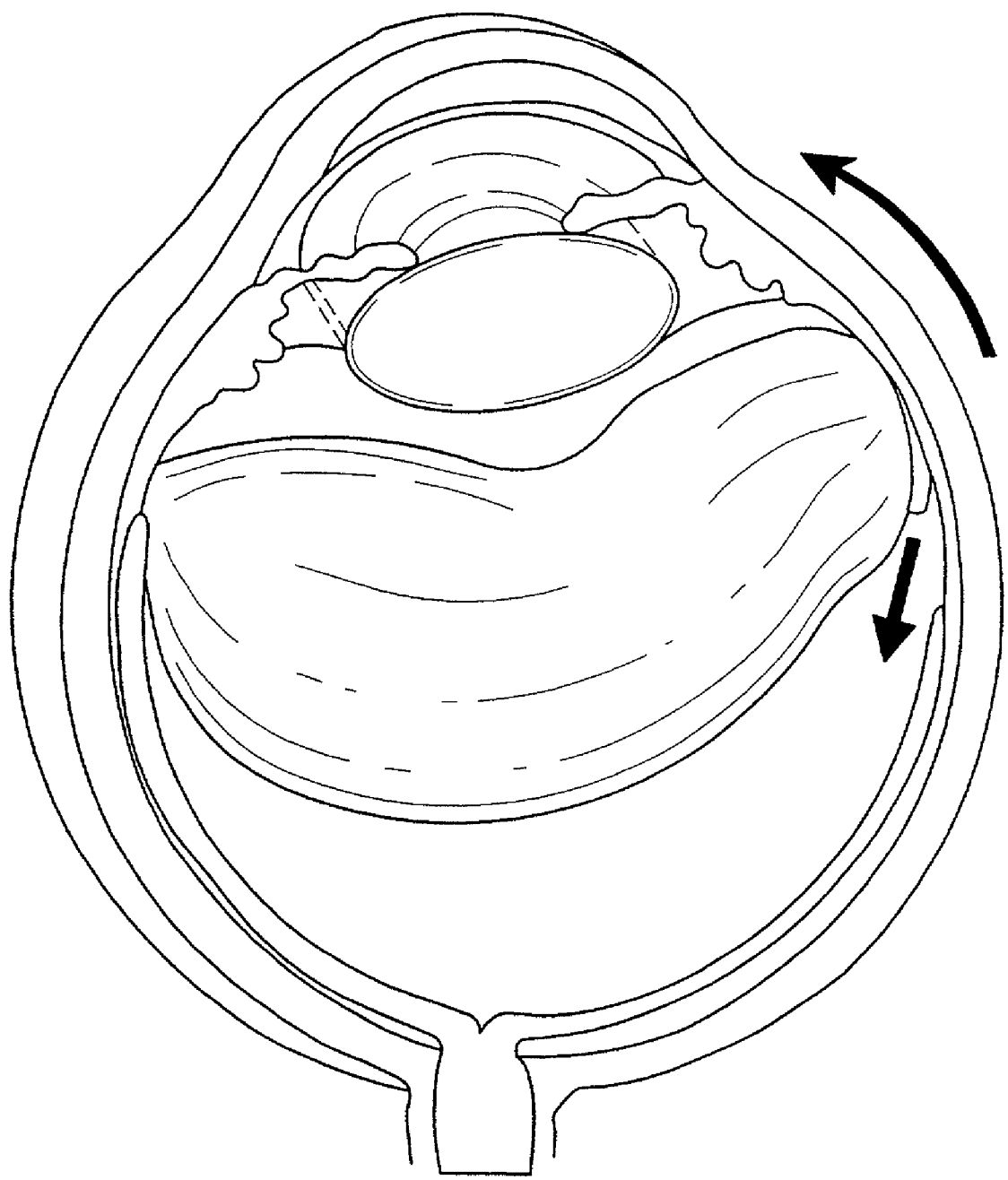
FIG. 5 illustrates vitreoretinal traction caused by eye movements. The direction of eye rotation is indicated by the arrow facing counter-clockwise. The clock-wise arrow indicates the direction of vitreoretinal drag and also points toward an accumulation of subretinal fluid. Immediately above the subretinal fluid is the vitreous gel.

Vitreoretinal traction has a number of causes, which range form simple action of gravitational force on the vitreous gel to prominent transvitreal fibrocellular membranes. Gravitational force is important and probably accounts for the high percentage of superior retinal tears (80%). However, rotational eye movements, which exert strong forces on all vitreoretinal adhesions, probably are more important causes or ongoing vitreoretinal traction[6]. When the eye rotates, the inertia of the detached vitreous gel causes it to lag behind the rotation of the eyewall and, therefore, the attached retina. The retina at the site of vitreoretinal adhesion exerts force on the vitreous gel, which causes the adjacent vitreous to rotate. The vitreous gel, because of its inertia, exerts an equal and opposite force on the retina, which can cause a retinal break or separate the neural retina further form the pigment epithelium if subretinal fluid is already present (FIG. 5). When the rotational eye movement stops, the vitreous gel continues its internal movement and exerts vitreoretinal traction in the opposite direction.

In addition to gravitational and inertial forces, vitreoretinal traction can be caused by contracture of intraocular fibroproliferative tissue associated with trauma, retinal vascular proliferative disorders, and other conditions. This type of traction does not always create a retinal break. Instead, a traction retinal detachment may be produced. There are classic features that often are used to differentiate this type of detachment form the rhegmatogenous variety[7]. Sometimes significant vitreoretinal traction initially causes a localized traction detachment, which later becomes more extensive with the development of a retinal break.

Liquid Currents

Figure 6:
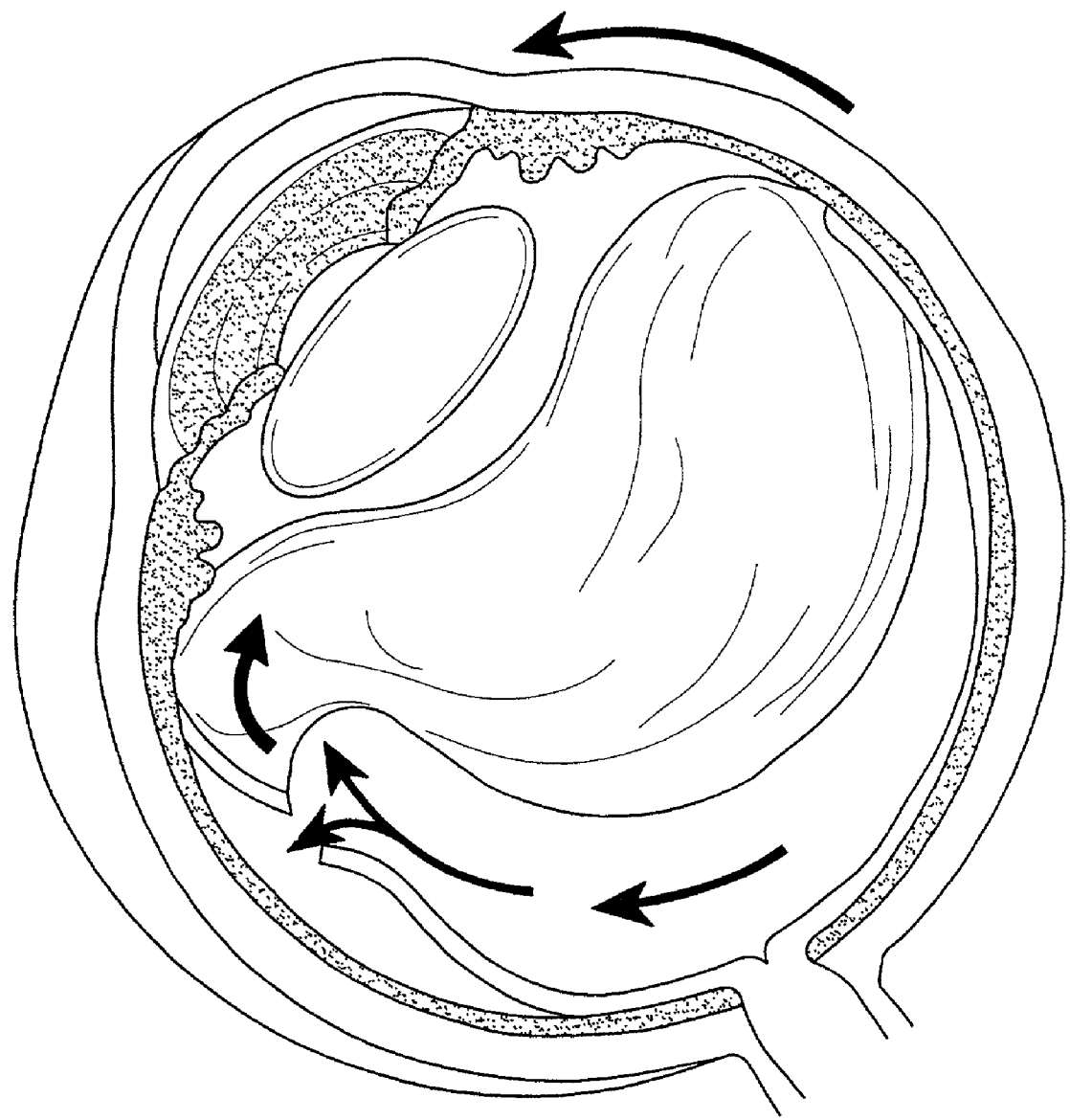
FIG. 6 illustrates the extension of retinal detachment associated with eye movements. The direction of eye rotation is indicated by the arrow facing counter-clockwise at the top of the figure. The arrows at the bottom of the figure facing clockwise indicate liquid pushing against vitreous gel adjacent to a retinal tear. Fluid is pushed through the retinal tear, as indicated by the two-headed clockwise facing arrow. The arrow pointing toward the top of the figure indicates liquid currents pushing against the vitreous gel.
Figure 7:
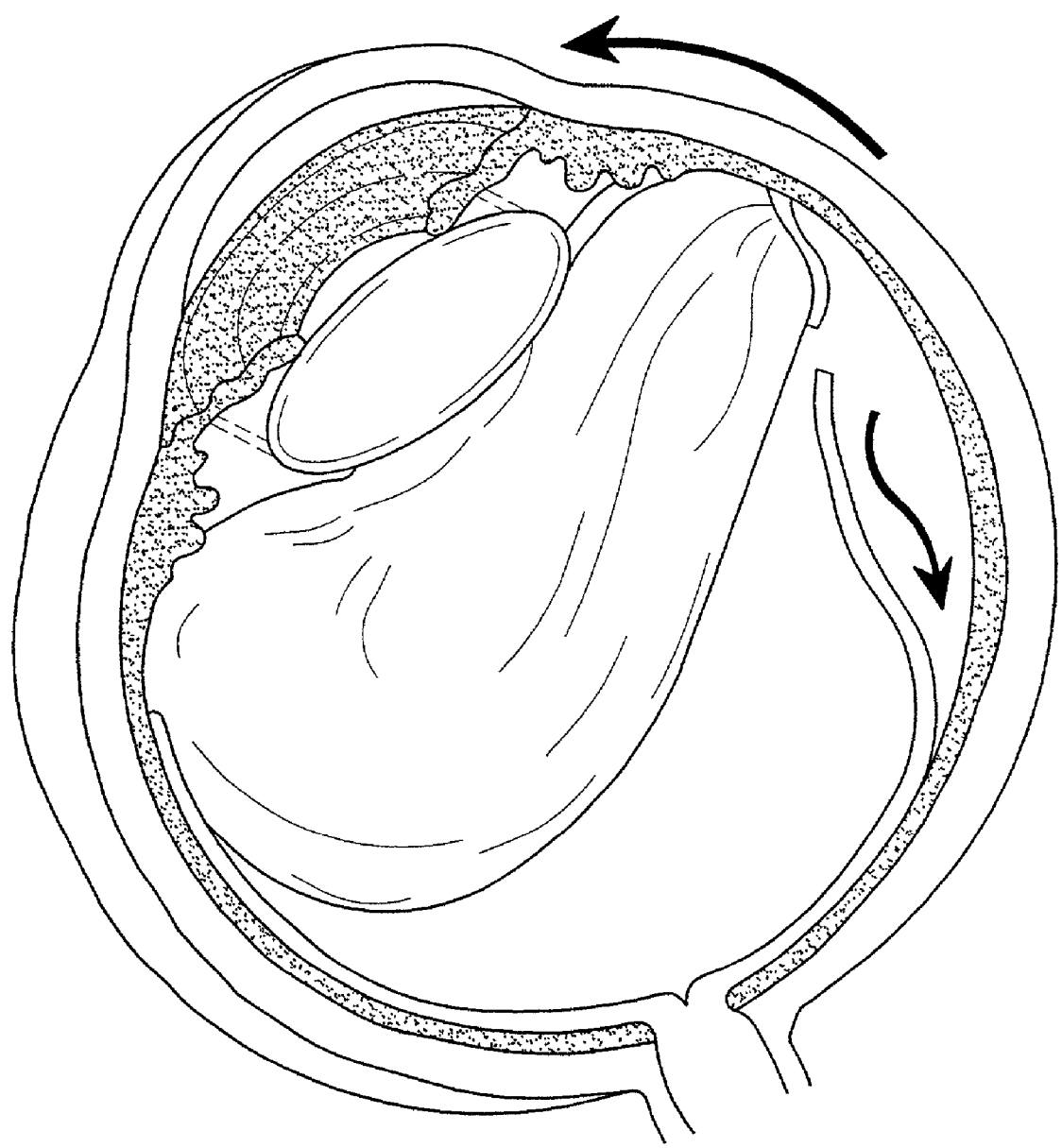
FIG. 7 illustrates the extension of subretinal fluid associated with eye movements. The direction of eye rotation is indicated by the arrow facing counter-clockwise. Subretinal fluid causes extended retinal detachment, as indicated by the downward facing arrow.

Continuous flow of liquid vitreous through a retinal break into the subretinal space is necessary to maintain a rhegmatogenous retinal detachment, because subretinal fluid is absorbed continually from the subretinal space via the RPE. This flow is encouraged by vitreoretinal traction, which tends to elevate the retina from the RPE. Rotary eye movements cause liquid currents in the vitreous to push against the gel adjacent to the retinal break and to dissect beneath the edge of retinal break into the subretinal space (FIG. 6). Subsequent eye movements also have an inertia effect on the subretinal fluid that favors extension of the retinal detachment (FIG. 7).

Conditions that Predispose an Eye to Retinal Detachment

Retinal detachments are relatively unusual in the general population the accepted annual incidence FIG. 1 approximately 1:10,000[8]. However, a variety of ocular and systemic disorders are associated with pathologic vitreous liquefaction, premature vitreous detachment, and extensive sites of vitreoretinal adhesion. These conditions, therefore, also are associated with increased chances of retinal detachment. Particularly important predisposing entities include high myopia, pseudophakia and aphakia, blunt and penetrating ocular trauma, and cytomegalovirus retinitis associated with acquired immunodeficiency syndrome.

Although cataract surgery has been performed on only approximately 3% of the general population, up to 40% of eyes with retinal detachment have had prior cataract surgery[9]. Retinal detachment represents the most significant potential post surgical complication of cataract surgery, as it occurs in nearly 1% of pseudophakic eyes[10]. Removal of the natural lens is believed to increase the risk of retinal detachment because of its effect on vitreous liquefaction and subsequent premature PVD[11]. The status of the posterior capsule determines the rapidity of vitreous liquefaction. It is clear that opening the posterior capsule, either surgically or with a neodymium:yttruim-aluminum-garnet laser, significantly increases the incidence of retinal detachment[12].

High myopia (>6.0D myopia) is associated with at least a threefold increased incidence of retinal detachment[13]. Severe ocular trauma is believed to be responsible for 10–15% of retinal detachments, and up to 50% of patients who have a diagnosis of cytomegalovirus retinitis develop a rhegmatogenous retinal detachment within 1 year[14].

Risk factors for retinal detachment are not mutually exclusive and may be additive. For example, prior cataract extraction and nonsurgical trauma are more likely to be complicated by retinal detachment in myopic eyes. Pathologic vitreoretinal changes often occur bilaterally—patients who have a retinal detachment in one eye usually have a substantially increased risk of retinal detachment in the fellow eye, provided that additional acquired risk factors are comparable.

The early symptoms of acute retinal detachment are the same as those of acute posterior vitreous detachment (PVD)—the sudden onset of tiny dark floating objects, frequently associated with photopsia (flashes). Photopsia flashes are usually brief, in the temporal visual field, and are best seen in the dark immediately following eye movement. Loss of visual field does not occur until sufficient fluid has passed through the retinal break(s) to cause a retinal detachment posterior to the equator. Retinal detachments with a relatively small amount of subretinal fluid (less than two disk diameters from the break) often are not accompanied by visual field loss; these are termed subclinical detachments. Rarely, but especially in young female myopes, asymptomatic retinal detachment can occur. This is most common inferiorly and usually occurs as a result of atrophic holes in lattice degeneration[15].

Figure 8A:
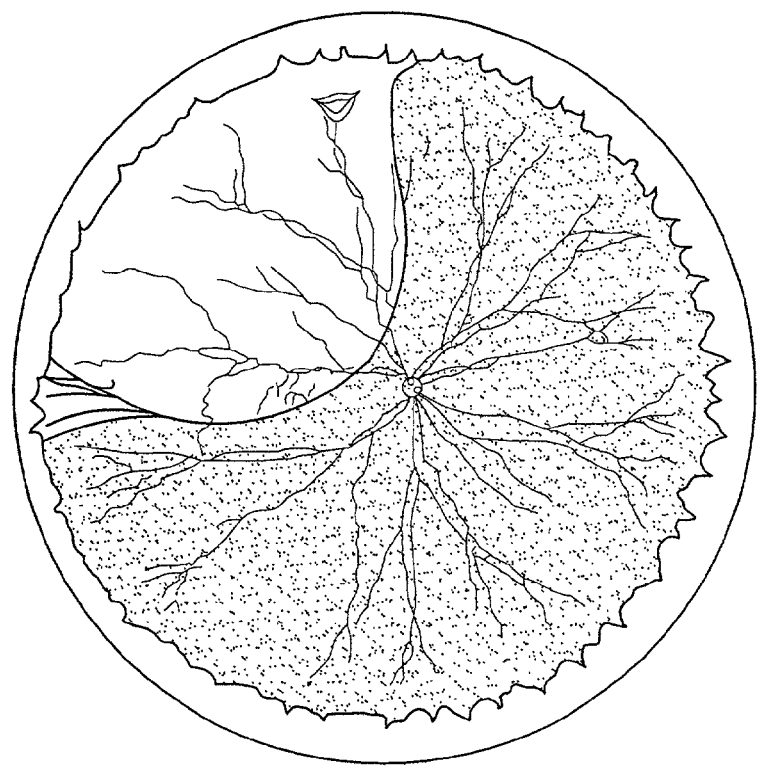
FIG. 8 illustrates superotemporal rhegmatogenous retinal detachments. In the top figure is shown a retinal detachment. The tear is at the top and center of the figure. An area of retinal detachment is shown in the upper left quadrant of the circular retina illustrated. In the bottom figure, the macular is shown by a darkened oval to the right of the center of the figure. The area of retinal detachment is shown in the bottom left quadrant of the graph.
Figure 8B:
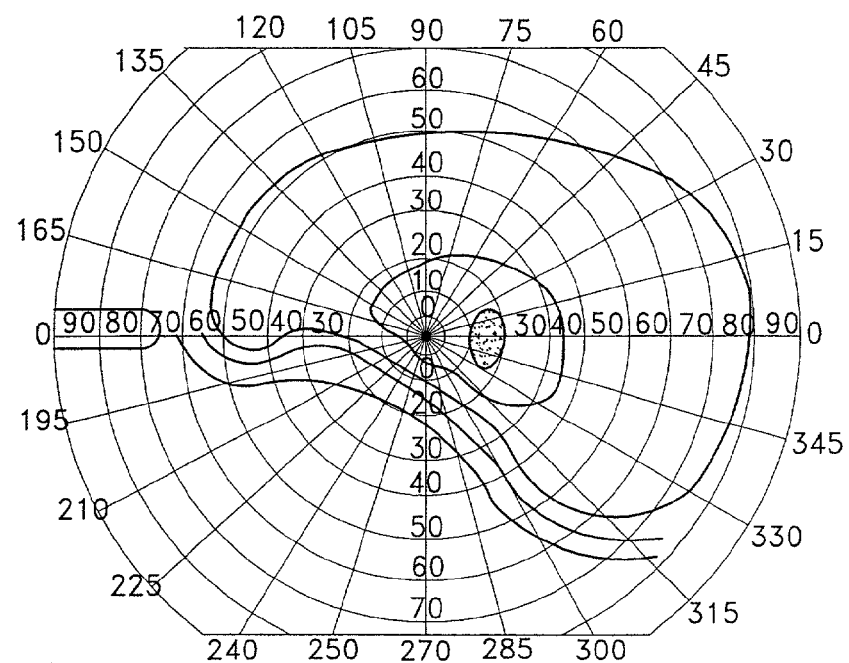

The vast majority of retinal breaks are located at the equator or more interiorly; subretinal fluid initially accumulates in the retinal periphery, where it causes a corresponding loss of peripheral vision in the area that is related inversely to the location of the retinal detachment (FIG. 8). The loss of peripheral vision (a 'curtain effect') increases as the detachment enlarges; central visual acuity is lost when subretinal fluid passes beneath the macula. Frequently, patients do not notice any symptoms until the macula becomes involved.

Retinal breaks associated with small amounts of subretinal fluid are difficult to detect; however, the diagnosis becomes more obvious as the retinal detachment increases in size. A stereoscopic vitreoretinal examination typically reveals an elevated sensory retina in the arc of detachment, but the critically important identification of all retinal breaks may remain difficult—it is considerable easier to diagnose the retinal detachment than to detect all retinal breaks.

Figure 9:
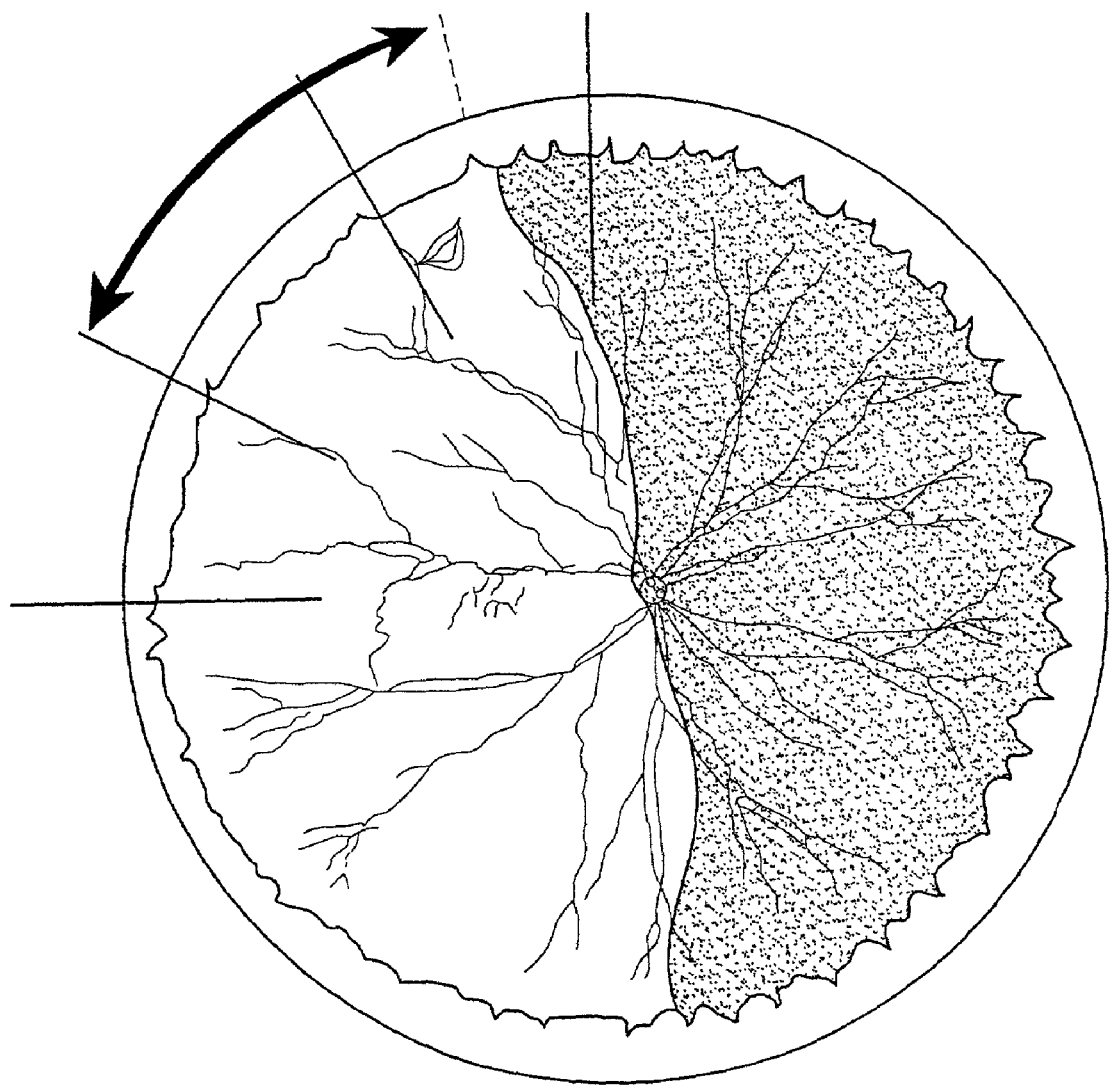
FIG. 9 illustrates a retinal detachment involving two quadrants of a retina. The area of retinal break is shown by the two-headed arrow.
Figure 10:
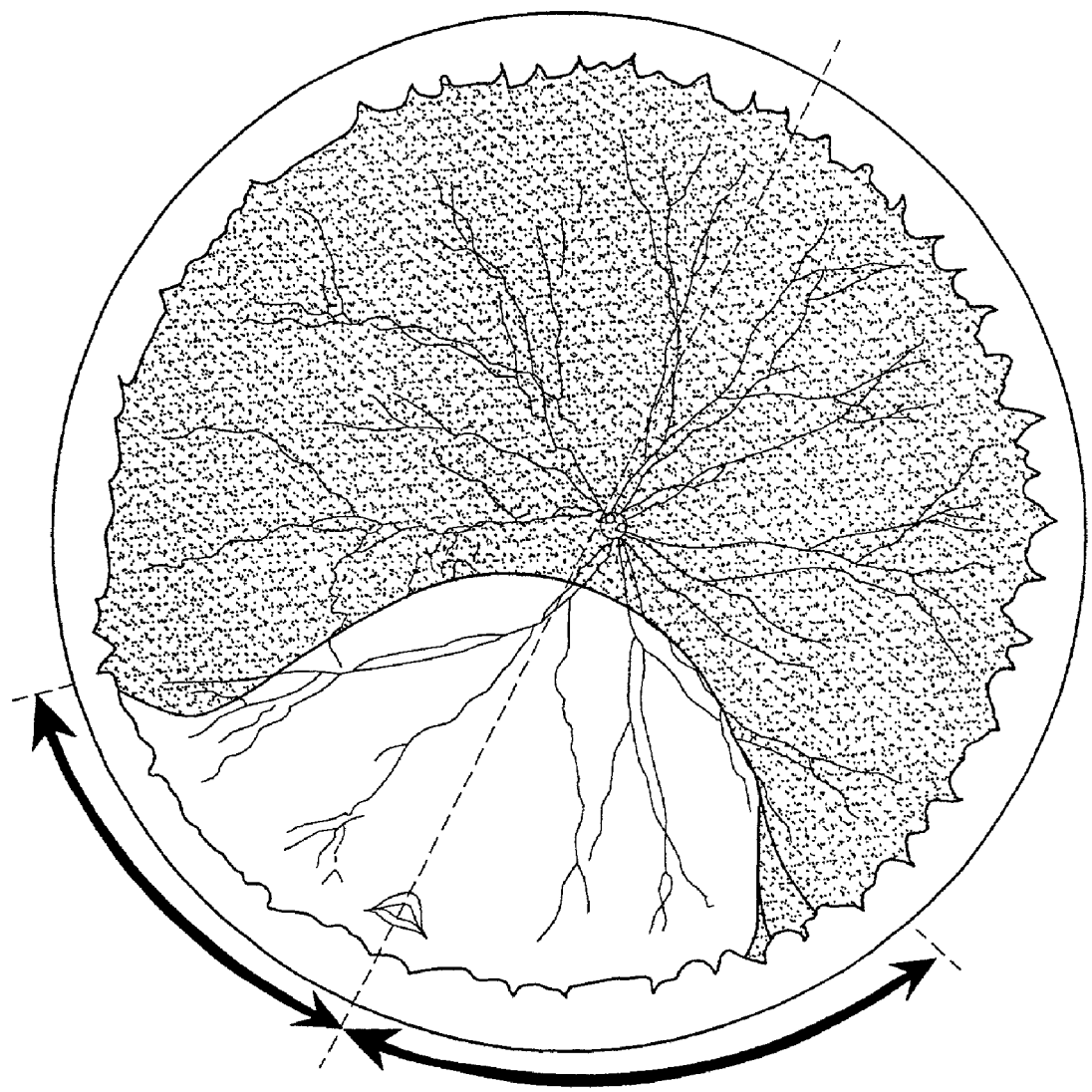
FIG. 10 illustrates a retinal detachment involving the lower quadrants of a globe. The area of retinal break is shown by the two two-headed arrows.

The effects of gravity mean that the topography of a retinal detachment is of major value in the prediction of the most likely locations of retinal breaks[16]. Retinal breaks usually are present superiorly within the area of detachment. Thus, if a retinal detachment involves one upper quadrant or both the superior and inferior quadrants on one side of the vertical meridian, the responsible retinal break is likely to be near the superior edge of the detachment (FIG. 9). Retinal detachments that involve the inferior quadrants tend to follow the same rules, but the progression of the detachment often is much slower, and symmetric spread of subretinal fluid may occur on both sides of the break. Therefore, detachments that involve on or both inferior quadrants may have a break near the superior margin of the detachment or in the meridian that bisects the area of detachment (FIG. 10). Nevertheless, since multiple retinal breaks are common, the entire periphery of the detached retina must be meticulously examined.

Repair and Regeneration

Although of neural origin, the retinal pigment epithelium (RPE) can be a plenipotential tissue. In amphibians, RPE cells can regenerate lens, neural retina, and other components of eye, this does not take place in humans. Nevertheless, the RPE is capable of local repair (unlike the neural retina) and cells may migrate and take on altered characteristics. After a laser bum, for example, the RPE cells that surround the burn begin to divide and small cells fill the defect to form a new blood—retinal barrier within 1–2 weeks[18]. In degenerative disease, such as retinitis pigmentosa, RPE cells migrate into the injured neural retina and sometimes come to rest around vessels to contribute to the characteristic bone spicule appearance. An overly vigorous RPE response can lead to duplicated layers of RPE cells and RPE scarring, which may be a part of a macular degenerative process. In the extreme, RPE cells contribute to proliferative vitreoretinopathy. Growth factors form the RPE may, at times, help contain unwanted proliferation, and at other times stimulate vascular or fibrous growth. Functionally, the most useful RPE repair characteristic is the ability to heal defects. The value to photocoagulation for macular edema and proliferative diabetic retinopathy may, in part, depend on the ability of RPE cells to seal laser scars, re-establish a degree of normal transport, and avoid unnecessary leakage of proteins into the subneural retinal space.

As illustrated by the discussion above, retinal detachments generally have negative connotations for the sight of the afflicted subject. Recently, however, it has been theorized that by intentionally detaching some or all of a subject's retina, and the relocating or reorienting the retina into a new configuration, can have certain positive ophthalmic results. In fact, retinal relocation therapy is contemplated to be efficacious in the treatment of a number of different conditions such as retinal diseases (retinopathy) including central serous retinopathy, diabetic retinopathy, ocular ischemic syndrome, photic retinopathy, bardet-biedl syndrome, post-infections, proliferative, purtscher's, radiation retinopathy, neovascularization of the angle, venous stasis, chorioretinopathy, retinopathy of prematurity, and retinopexy are all contemplated for treatment with the methods and compounds described herein.

A major problem with retinal relocation therapy is that the retina is difficult to detach and relocate without causing unintended complications to the retinal space of the treated eye. Additionally, physical manipulation of a detached retina often results in degradation of the detached retinal tissue, which in turn reduces the efficacy of the retinal relocation therapy. The methods of the invention disclosed herein solve these problems. In the presence of a short chain polymeric alcohol, such as polyethylene glycol (PEG), or another retinal detachment agent, the retina of a subject is induced to detach from the retinal matrix holding the retina on the eye without damaging the eye or the detached retinal tissue.

Without being bound to any particular theory, the detachment of retinal tissue from a subject's eye has been induced by the application of short chain polymeric alcohols, such as polyethylene glycol (PEG). The use of such compounds permits the selective detachment of a retina in a subject. Once detached, the retina can be relocated to a second position at which retinal reattachment can occur.

The methods of the invention disclosed herein are capable of providing a number of advantages over traditional surgical methods of retinal detachment. For example, the incidence of cell release into the vitreal space is greatly reduced when retinal detachment is induced using the methods disclosed herein. Also, the integrity of the retinal tissue following reattachment is substantially less impaired when the non-surgical detachment method of the invention disclosed herein is used.

As discussed above, the vitreous humor is attached to the retina in several locations. Vitreoretinal traction resulting from these interaction often produces tears in detached retinal tissue. Accordingly, reduction or removal vitreoretinal traction will help to preserve the integrity of a detached retina. In one embodiment, retinal integrity is protected following detachment by administering hyaluronidase to liquefy the vitreous humor. Vitreal liquefaction is taught in U.S. Pat. No. 5,866,120, which is hereby incorporated by reference.

A Preferred Hyaluronidase Preparation for Ophthalmic Administration

A general formulation for an injectable, thimerosal free hyaluronidase preparation of the present invention is shown in Table 1 and Table 2 as follows.

TABLE 1

General Formulation

| Ingredient | Quantity |
| --- | --- |
| Hyaluronidase ACS | Up to 8000 International Units |
| Lactose USP | 5.0 mg–130.0 mg |
| Phosphate USP | 0.01–100 mmoles |

These formulation ingredients are initially dissolved in sterile water, sterile filtered and subsequently lyophilized to a dry composition. The lyophilized composition is packaged for subsequent reconstitution prior to use; in a suitable solvent such as sterile isotonic saline solution or balanced salt solution.

TABLE 2

Liquid Formulation

| Ingredient | Quantity (w/v) |
| --- | --- |
| Liquid Formulation in a Sterile 3.0 ml Glass Vial-0.3 ml Fill Volume | |
| Hyaluronidase ACS | 1500 I.U./ml |
| Lactose USP | 1.25 mg/ml |
| Potassium Phosphate Monobasic USP | 0.305 mg/ml |
| Potassium Phosphate Dibasic USP | 0.48 mg/ml |
| Sodium Chloride USP | 9.0 mg/ml |
| Water for Injection USP | Q.S. |
| Liquid Formulation in a Sterile Pre-filled Syringe-0.15 ml Fill Volume | |
| Hyaluronidase ACS | 1500 I.U./ml |
| Lactose USP | 1.25 mg/ml |
| Potassium Phosphate Monobasic USP | 0.305 mg/ml |
| Potassium Phosphate Dibasic USP | 0.48 mg/ml |
| Sodium Chloride USP | 9.0 mg/ml |
| Water for Injection USP | Q.S. |

The biochemical method for inducing a retinal detachment in the eye of a subject mammal without retinal surgery is achieved by injecting into the subject vitreous a glycol ether or a glycol ether derivative. In this regard, applicant has devised a method for a non-surgical retinal detachment, said method further comprising the step of contracting the vitreous with at least one enzyme in an amount, which is active to accelerate the liquefaction of the vitreous. This vitreous liquefaction of the present invention may be performed without any other surgical manipulation or vitrectomy, thereby avoiding the potential risks and complications associated with vitrectomy.

Specific glycosaminoglycanase enzymes that exhibit this vitreous liquefying effect include: hyaluronidase; hexosaminidase; endo-β-glucuronidase; keratinase; chondroitinase ac; chondroitinase b; chondroitinase abc; and chondroitin 4 sulfatase and chondroitin 6 sulfatase.

Specific metalloproteinase enzymes that exhibit this vitreous liquefying effect include: matrix metalloproteinase-1; matrix metalloproteinase-2; matrix metalloproteinase-3; and matrix metalloproteinase-9.

Specific protein-kinase enzymes that exhibit this vitreous liquefying effect include: streptokinase and urokinase.

Many kinds of hyaluronidase enzyme free of thimerosal preservative can be used, however, the term "hyaluronidase ACS" as used here describes a preferred hyaluronidase which the applicants have determined to result in less ophthalmic toxicity than other hyaluronidase preparations while exhibiting desirable therapeutic efficacy in a number of ophthalmic applications.

The hyaluronidase (ACS) of the present invention, and/or the exclusion of thimerosal form its formulation, provides a hyaluronidase preparation which is non-toxic to the eye when administered at dosage levels at which other hyaluronidase preparations preserved with thimerosal would cause toxic effects.

The induction of a retinal detachment in the present invention is achieved by injecting glycol ether or a glycol ether derivative into the vitreous. The said method generally is comprised of the steps of contracting, with the vitreous humor, a quantity of glycol ether or glycol ether derivative at a dose, which is insufficient to accelerate the detachment of the retina temporarily, without causing damage to the retina or other tissues of the eye.

The methods of non-surgical retinal detachment disclosed herein are applicable mammalian eyes. It is readily apparent to those of skill in the art that a wide variety of mammalian organisms could benefit from the methods disclosed herein.

Administration

Preferably the retinal detachment compounds are administered intravitreally. In one embodiment, the route of retinal detachment compound administration is by intraocular injection directly into the vitreous body. Other routes of for the administration of retinal detachment compounds are contemplated. In fact, any other suitable route of administration that results in the distribution of the retinal detachment compound to the vitreous body to cause retinal detachment is encompassed by the invention disclosed herein.

Regarding volumes of administration, one of ordinary skill in the art would be aware that the total volume of liquid administered to an eye is limited by the amount of pressure generated by the administration. The volume of the composition administered to an eye using the methods described herein is not to exceed a volume that would create a detrimental amount of intraocular pressure. Typically, a volume range from about 1 to 250 µl is administered. Preferably a range from about 25 to 100 µl is administered. More preferably, about 50 µl is administered.

Retinal Detachment Compounds

A number of retinal detachment compounds are contemplated for use in the disclosed invention. Such compounds include, but are not limited to short chain polymeric alcohols having 1 to 4 (e.g., polyethylene glycol), glycol ethers and glycol ether derivatives.

Specific glycol ether and glycol ether derivatives and the like that exhibit the retinal detachment effect include: polyethylene-propylene glycol copolymers such as poloxamer 124, 188, 237, 338, 407; polyethylene glycol: polyoxyethylene glycol, peg 200, 300, 400, 540, 600, 900, 1000, 1450, 1540, 2000, 3000, 3350, 4000, 4600, 8000, 20000; polyethylene glycol (40) monostearate; polyethylene glycol (50) monostearate; polyethylene glycol (400) monostearate; polyethylene glycol (400) distearate; polyethylene glycol trimethylnonyl ethers; peg-4 laurate; peg-6 laurate; peg-6 oleate; peg-5 stearate; peg-8 stearate; peg 10 propylene glycol glyceryl laurate; polyoxyethylene alkyl ethers, such as: poloxyl 20 cetostearyl ethers and brij 52, 56, 58, 30, 35, 92, 96, 98, 72, 76, 78, 700; polyoxyethylene castor oil derivatives, such as: poloxyl 5 castor oil, p-9 castor oil, p-15 castor oil, p-40 castor oil, p-40 hydrogenated castor oil, p-60 hydrogenated castor oil; polyoxyethylene sorbitan fatty acid esters, such as: polysorbate 20, 21, 40, 60, 61, 65, 80, 81, 85, 120; polyoxyethylene stearates, such as: polyoxyl 2 stearate, p-6 stearate, p-8 stearate, p-12 stearate, polyoxyl 20 stearate, p-30, p-40, p-50, p-100, p-150 stearates; and polysorbate 20.

The preferred injectable retinal detachment compound containing solutions may contain retinal detachment compounds at doses of about 0.1, 1, 5, 10, 15, 20, 25, 30, 35, 40, 45, 50, 55, 60, 65, 70, 75, 80, 85, 90, 95, or about 100% w/v. Polyethylene Glycol 300, without causing toxic damage to the eye, along with inactive ingredients, which cause the solution to be substantially isotonic or hypertonic, and a pH, is suitable for injection into the eye. This glycol ether preparation is preferably devoid of any preservative. Such solution for injection may be in the form of a sterile solution, or could be in a pre-filled syringe ready to be injected into the eye.

A Preferred Glycol Ether Preparation for Ophthalmic Administration

General formulations for injectable polyethylene glycol 300 preparations are shown in the following tables.

TABLE 3

General Formulation

| Ingredient | Quantity |
| --- | --- |
| Polyethylene Glycol 300 USP | 100% w/v |

TABLE 4

Preferred Formulation

| Ingredient | Quantity |
| --- | --- |
| PEG 300 USP | 50% w/v |
| Sterile Isotonic Saline USP | 50% w/v |

TABLE 5

Preferred Formulation

| Ingredient Quantity | Quantity |
| --- | --- |
| PEG 300 USP | 75% w/v |
| Water for Injection USP | 25% w/v |

A general formulation for an injectable polyethylene glycol 400 preparation of the present invention is shown in the following tables.

TABLE 6

General Formulation

| Ingredient | Quantity |
| --- | --- |
| Polyethylene Glycol 400 USP | 100% w/v |

TABLE 7

Preferred Formulation

| Ingredient | Quantity |
| --- | --- |
| PEG 400 USP | 50% w/v |
| Sterile Isotonic Saline USP | 50% w/v |

TABLE 8

Preferred Formulation

| Ingredient Quantity | Quantity |
| --- | --- |
| PEG 400 USP | 75% w/v |
| Water for Injection USP | 25% w/v |

Suitable choices and amounts of a particular retinal detachment compound for use in the methods described herein can easily be determined by one of ordinary skill in the art, for example, by performing the experiments described in Example 1 and applying scientific methodology to test variables while running appropriate controls.

Retinal Reattachment

A variety of methods are contemplated to reattach a detached retina. In one embodiment of the invention, the retinas detached using the methods of the disclosed invention spontaneously reattach. In another embodiment, the detached retinas are reattached using cryotherapy (cryopexy), photocoagulation, and diathermy. Additional methods of reattachment using laser induced scleral shrinkage and transscleral photocoagulation to facilitate retinal reattachment are taught in U.S. Pat. No. 5,688,264, which is hereby incorporated by reference. Retinal reattachment and retinal tissue protection are promoted by the administration of the compositions discussed herein.

Particular aspects of the invention may be more readily understood by reference to the following examples, which are intended to exemplify the invention, without limiting its scope to the particular exemplified embodiments.

EXAMPLE 1

Determination of Suitable Retinal Detachment Compounds and Concentrations Thereof Twelve (12) pigmented rabbits were divided into 2 groups of 6 animals each. Group I consisted of six animals that were injected OD with 50 μl of PEG 300 at 1, 10, 20, 50, 75, and 100% w/v. As a control, these same animals received saline injections OS and thus served as a control group. The effects of these injections were monitored using standard ophthalmic methods suitable to determine the health of the eye so injected as well as adapted to determine the extent of retinal detachment. These methods including light microscopy, electroretinography, and ultrasonography techniques were used to objectively determine the presence of retinal detachment.

EXAMPLE 2

Ophthalmic Toxicities of Thimerosal Hyaluronidase (ACS) and Hyaluronidase (Wydase®) in Rabbits Fifty-two (52) healthy rabbits of the New Zealand Cross variety (26 male, 26 female) weighing 1.5 kg to 2.5 kg were individually marked for identification and were housed individually in suspended cages. The animals received a commercially available pelleted rabbit feed on a daily basis, with tap water available ad libitum.

The animals were divided into thirteen groups of 4 animals each (2 males, 2 females). Two animals in each group (1 male, 1 female) were selected for pretreatment fundus photography and fluorescein angiography.

The fundus photography was performed by restraining the animals and visualizing the optic nerve, retinal arcades and fundus with a KOWA® RC-3 Fundus Camera loaded with Kodak Gold 200 ASA film.

The fluorescein angiography involved a 1.5-ml injection of 2% sterile fluorescein solution via the marginal ear vein. Approximately 30 seconds post-injection the fluorescein was visualized upon localization of the optic nerve, retinal vessels and fundus.

The following day, each animal was anesthetized by intravenous administration of a combination of 34 mg/kg of ketamine hydrochloride and 5-mg/kg xylazine. The eyelids were retracted using a lid speculum, and the eyes were disinfected with an iodine-povidone wash.

Experimental treatments of either balance salt solution (BSS), BSS+thimerosal, (Wydase®) or hyaluronidase (ACS) were administered by injection using a 1 cc tuberculin syringe with a 30 gauge, 0.5 inch needle attached thereto. The hyaluronidase (ACS) solution utilized in this example was free of thimerosal and constituted the specific preferred hyaluronidase (ACS) formulation set forth in Table II here above. The experimental treatments administered to each animal group were as follows:

TABLE 9

| Group # | Treatment |
|---|---|
| 1 | BSS |
| 2 | BSS + 0.0075 mg Thimerosal |
| 3 | BSS + 0.0025 mg Thimerosal |
| 4 | Hyaluronidase (Wydase) 1 IU |
| 5 | Hyaluronidase (Wydase) 15 IU |
| 6 | Hyaluronidase (Wydase) 30 IU |
| 7 | Hyaluronidase (Wydase) 50 IU |
| 8 | Hyaluronidase (Wydase) 150 IU |
| 9 | Hyaluronidase (ACS) 1 IU |
| 10 | Hyaluronidase (ACS) 15 IU |
| 11 | Hyaluronidase (ACS) 30 IU |
| 12 | Hyaluronidase (ACS) 50 IU |
| 13 | Hyaluronidase (ACS) 150 I.U. |

The day following the injections (Day 1) the 26 animals, which were subjected to the fundus photography and fluorescein angiography, were observed using the same methods as for the pre-dose examination.

On Day 2 following the injections, the 13 male rabbits that had received the fundus photography and fluorescein angiography at pre-dose and Day 1, as well as the 13 female rabbits that were not selected for photography were euthanized with a sodium pentobarbital drug. The eyes were then surgically removed and placed in a fixture solution of 2.5% glutararaldehyde with 0.1M phosphate buffered saline at pH 7.37. Alternatively, one randomly selected rabbit was euthanized by pentobarbital injection but then fixed by intracardiac injection of the gluteraldehyde solution into the left ventricle to determine the effect of the fixation procedure on the histology findings within the enucleated eyes.

On Day 7, the 13 female rabbits that had been previously photographed and angiography performed were subjected to same observations following the methods previously described.

The remaining 26 animals were euthanized as described above 7 days after dosing. The eyes were fixed in the same manner as those, which had been fixed on day 2. Also, one randomly selected rabbit was subjected to the same intracardiac gluteraldehyde fixation procedure described here above for the previously randomly selected animal.

The eyes of the animals treated in this example were examined grossly and microscopically for evidence of treatment-related toxicities.

In summary, the eyes of the BSS-treated control group were free of toxicity at 2 and 7 days post dose.

The eyes of the Group No. 2 animals treated with BSS+ thimerosal (0.0075 mg) were free of toxicity at day 2, but exhibited evidence that there was a breakdown of the blood retinal barrier at day 7.

The Group No. 3 animals treated with BSS+thimerosal (0.025 mg) exhibited severe treatment-related toxic effects, at day 2 and 7 post dose.

The Group No. 4 animals treated with Wydase® at the 1 IU dose were free of toxicity at days 2 and 7, however, the eyes of the animals in Group Nos. 5–8 treated with Wydase® at dosages ranging from 15 IU-150 IU exhibited generally dose-related toxic effects at days 2 and 7 post dose.

The eyes of animals in treatment Groups Nos. 9–13 treated with hyaluronidase (ACS) at dosages ranging from 1 IU through 150 IU, were free of evidence of toxic effects at days 2 and 7 post dose.

EXAMPLE 3

Ophthalmic Toxicities of Thimerosal, Hyaluronidase and Hyaluronidase (Wydase®) Injected in Rabbit Corneas Twenty (20) healthy rabbits of the New Zealand cross variety weighing 1.5 kg to 2.5 kg, were individually marked for identification and were hosed individually in suspended cages. The animals received a commercially available pelleted rabbit feed on a daily basis, with tap water available ad libitum.

The animals were divided into 4 groups of 5 animals each. All 20 animals were examined pre-treatment by slit lamp biomicroscopy and fluorescein staining for pre-treatment health of the rabbit corneas.

The following day, each animal was anesthetized by intravenous administration of a combination of 34 mg/kg of ketamine hydrochloride and 5-mg/kg xylazine. The eyelids were retracted using a lid speculum, and the eyes were disinfected with an iodine-povidone wash.

Experimental treatments of either balanced salt solution; Hyaluronidase (Wydase®) or Hyaluronidase (ACS) was administered by injection using a 0.3 cc tuberculin syringe with a 29 gauge, 0.5-inch needle attached thereto. The hyaluronidase (ACS) solution utilized in this example was free of thimerosal and constituted the specific preferred hyaluronidase ACS formulation set forth in Table 2.

The experimental treatments administered to each animal group were as follows:

| | TREATMENT | |
|---|---|---|
| GROUP NO. | Right Eye | Left Eye |
| 1 | BSS | Untreated control |
| 2 | Hyaluronidase (Wydase) 25 I.U. | Hyaluronidase (Wydase) 100 I.U. |
| 3 | Hyaluronidase (ACS) 25 I.U. | Hyaluronidase (ACS) 100 I.U. |
| 4 | Hyaluronidase (ACS) 500 I.U. | Hyaluronidase (ACS) 1000 I.U. |

On days 1, 7, 15, and 30 following the injections, the eyes of the animals were examined grossly and biomicroscopically for evidence of treatment related toxicities.

In summary, the eyes of the BSS treated and untreated control groups were free of toxicity.

The eyes of Group 2 animals treated with Hyaluronidase (Wydase®) preserved with thimerosal were found to be toxic.

The eyes of Group 3 and Group 4 animals treated with Hyaluronidase (ACS) were found to be free of toxicity.

Accordingly, it is concluded that thimerosal containing Wydase® formulation does cause toxic effects in the eyes of rabbits at the dosages tested. However, hyaluronidase (ACS) caused no toxic effects for these animals at the dosages tested.

Creation of retinal detachment is an essential component of macular translocation. Presently retinal detachment is created using mechanical methods that cause damage to the integrity of the retina as well as the appearance of Proliferative Vitreoretinopathy (PVR). Proliferative Vitreoretinopathy is the most common cause of ultimate failure after surgical treatment for rhegmatogenous retinal detachment[17, 18]. PVR is characterized by epiretinal and subretinal fibrous proliferation, contraction of membranes, recurrent retinal detachment, reopening of pre-existing retinal breaks and formulation of new retinal breaks. Other associated features of PVR are hypotory, vitreous opacity, aqueous flare, iris neovascularization and macular pucker.

EXAMPLE 4

Induction of Reversible Retinal Detachment in Rabbits for Retinal Translocation using PEG 300 and PEG 400

In this study, 12-pigmented rabbits were divided into 2 groups of 6 animals each. Group I consisted of six animals that were injected OD with PEG 300. Each of the animals received were first injected intravitreally 50μl of 75 I.U. of hyaluronidase (ACS). Three days after the administration of hyaluronidase, the animals received 50 μl of PEG 300. As a control, these same animals received saline injections OS and thus served as a control group (Group Ia).

Group II consisted of six animals that were injected that were injected OD with PEG 400. As with Group I, each of the animals received were first injected intravitreally 50 μl of 75 I.U. of hyaluronidase (ACS). Three days after the administration of hyaluronidase, the animals received 50 μl of PEG 400. As a control, these same animals received saline injections OS and thus served as a control group (Group IIa).

During this procedure a number of ophthalmic methodologies were utilized to monitor the effects and progress of the various experimental treatments. For example, indirect ophthalmoscopy was utilized by a retinal specialist to determine the effects of administering a retinal detaching dose of the compounds disclosed. Fundus photography was used to document the effects of the treatments, in addition to document the retinal detachment as well as the spontaneous retinal re-attachments. Light microscopy and electron microscopy of eye samples was used to determine the effect of the treatments from a histological perspective. Ultrasonography techniques were used to objectively determine the presence of retinal detachment. Additionally, electroretinography was performed to determine changes due to treatment. The observed results of this experiment are summarized in Table 10.

The results show that animal injected first with 75 I.U. of Hyaluronidase enzyme solution followed 3 days later with a second intravitreal injection of PEG 300 or PEG 400 induced retinal detachment in the rabbit eyes within 48 hours. The detached retinas spontaneously re-attached within 3 weeks of the intravitreal injection of PEG 300 and PEG 400. The control group that received the sterile saline solution did not produce any retinal detachments. The intravitreal injection of Hyaluronidase followed by the intravitreal injection of PEG 300 and PEG 400 was determined to be safe by using measurement techniques, like Indirect Ophthalmoscopy, Fundus Photography, Light and Electron Microscopy and Electroretinography.

Efficacy of inducing retinal detachments and retinal re-attachments were documented by Indirect Ophthalmoscopy, Fundus Photography and Ultrasonography (β-Scan).

The results in this experiment show that PEG 300 and PEG 400 injected intravitreally are safe and effective in inducing retinal detachment in 48 hours and within 3 weeks retinal re-attachment without causing any toxicity.

TABLE 10

Induction of Reversible Retinal Detachment in Rabbits for Retinal Translocation using PEG 300 and PEG 400

| Rabbit Group Number | 1st Intravitreal Injection | 2nd Intravitreal Injection | Retinal Detachment at 48 hours Post 2nd Injection | Retinal Reattachment at 3 weeks Post 2nd Injection | Electro Retinography Results | Histological and Electron Microscopic Results |
|---|---|---|---|---|---|---|
| Group I Treatment n = 6 | 50 μl of 75 I.U. of Hyaluronidase solution | 50 μl of sterile PEG 300 | All Fundus Photos β Scans | All Fundus Photos β Scans | Normal No Adverse Effects | Normal No Histological Changes Observed |
| Group Ia Control n = 6 | 30 μl of 75 I.U. of Hyaluronidase solution | 50 μl of sterile saline solution | None Fundus Photos β Scans | Not Applicable Fundus Photos β Scan | Normal | Normal |
| Group II Treatment n = 6 | 50 μl of 75 I.U. of Hyaluronidase solution | 50 μl of sterile PEG 400 | All Fundus Photos β Scans | All Fundus Photos β Scans | Normal No Adverse Effects | Normal No Histological Changes Observed |
| Group IIa Control n = 6 | 30 μl of 75 I.U. of Hyaluronidase solution | 50 μl of sterile saline solution | None Fundus Photos β Scans | Not Applicable Fundus Photos β Scan | Normal | Normal |

EXAMPLE 5

Induction of Reversible Retinal Detachment in Rabbits for Retinal Translocation using Varying Concentration of PEG 300

In this study, 8-pigmented rabbits were divided into 4 groups of 2 animals each. Group I consisted of 2 animals The observed results in this experiment are summarized in Table 11. The results show that animals injected with 75 I.U. of Hyaluronidase enzyme solution followed 14 days later with a second Intravitreal Injection of varying concentrations of PEG 300 induce retinal detachment in rabbit eyes within 48 hours. The detached retinas spontaneously re-attach within 3 weeks of the PEG injection. The control group does not produce any retinal detachment.

TABLE 11

Induction of Reversible Retinal Detachment in Rabbits for Retinal Translocation using PEG 300

| Rabbit Group Number | 1st Intravitreal Injection | 2nd Intravitreal Injection | Retinal Detachment At 48 hours Post 2nd Injection | Retinal Reattachment At 3 weeks Post 2nd Injection | Electro Retinography Results | Histological and Electron Microscopic Results |
|---|---|---|---|---|---|---|
| Group I - OD 100% PEG 300 | 30 µl of 75 I.U. of Hyaluronidase solution | 50 µl of sterile 100% PEG 300 | All Fundus Photos β Scans | All Fundus Photos β Scans | No Adverse effects were observed in the Electro-retinography results after retinal detachment and spontaneous retinal re-attachments 3 weeks later. | No Adverse Histological or Electron Microscopy changes were observed on 3 years that were enucleated and prepared for light and Electron Microscopy. |
| Group II - OD 75% PEG 300 | | 50 µl of sterile 75% PEG 300 | | | | |
| Group III- OD 50% PEG 300 | | 50 µl of sterile 50% PEG 300 | | | | |
| Group IV - OD 25% PEG 300 | | 50 µl of sterile 25% PEG 300 | | | | |
| Group Ia - OS Untreated Control | None | None | None Fundus Photos β Scans | Not Applicable Fundus Photos β Scan | Normal | Normal |
| Group IIa -OS Untreated Control | | | | | | |
| Group IIIa - OS Untreated Control | | | | | | |
| Group IVa - OS Untreated Control | | | | | | | treated with 100% PEG 300. As performed in Example 1, these animals were first injected intravitreally (OD) with 50 µl of 75 I.U. of Hyaluronidase solution (Group I). Fourteen days after the first injection these animals received 50 µl of 100% sterile PEG 300 intravitreally. The OS eye was used as the untreated control as described in Example 1 (Group Ia). A second group of two animals, Group II, was first injected intravitreally (OD) with 50 µl of 75 I.U. of Hyaluronidase solution and then injected 14 days later with 50 µl of sterile 75% solution of PEG 300 intravitreally. The OS eyes of these animals were used as the untreated controls (Group IIa). Groups II and IIa were treated according to the same protocols as described for Groups I, Ia, II, and IIa with the exception that Group III received 50 µl of 50% sterile solution of PEG 300 intravitreally. Similarly, Groups IV and IVa were treated according to the same protocols as described above, however, Group IV received 50 µl of 25% sterile solution of PEG 300 intravitreally.

All animals were observed at day 1 and 2, weeks 1, 2, 3 and 4 by Indirect Ophthalmoscopy and Fundus Photography. All retinal detachments and retinal re-attachments were documented using Fundus Photography and Ultrasonography (β-Scan). In addition, 3 rabbit eyes were enucleated and the eyes were prepared for light microscopy as well as for Electron Microscopy.

The intravitreal injection of Hyaluronidase followed the intravitreal injection of PEG 300 was determined to be safe. The efficacy of inducing retinal detachment and spontaneous retinal re-attachment was demonstrated at PEG 300 concentrations of 100%, 75%, 50% and 25% in saline vehicle respectively without causing any toxicity.

EXAMPLE 6

Retinal Detachment Reversal in Adult Cats Using Hyaluronidase

The study is performed on 15 adult cats (*Felis domesticus*) and modeled generally on the study of Mervin, et al., "Limiting Photoreceptor Death and Deconstruction During Experimental Retinal Detachment: The Value of Oxygen Supplementation," Am. J. Ophthal. 128:155–164 (1999). Unlike the Mervin study however, the present experiment examines the effect of hyaluronidase administration to prevent photoreceptor death rather than the effect of supplemental oxygen administration.

Three groups of five adult domestic cats (Experimental Group I, Experimental Group II, and Control Group I) are anesthetized using 10 mg/kg of xylazine (Boehringer Ingelheim Vetmedica, Inc., St. Joseph, Mo.) and 50 mg/kg of ketamine (Sigma, St. Louis, Mo.). The surgical method of Anderson, et al., (Invest. Ophthalmol. Vis. Sci. 27:168–183 (1986)) is used to induce retinal detachment in two experimental groups of 5 cats each, however, the lens and vitreous of these cats are left in place during the surgical procedure.

During the procedure, a glass micropipette is introduced through a 20-gauge hole in the sclera at the region of the pars plana. A balanced salt solution (BSS) containing 0.25% sodium hyaluronate is then infused between the neural retina and retinal pigment epithelium. A single detachment is produced in the right eye of each of the 10 cats.

The experimental groups are allowed to recover for six hours. The cats of Experimental Group I receive 100 μl of the PEG formulation described in Table 5 following the recovery period, while the cats of Experimental Group II and Control Group mH receive no PEG. The animals are then housed for 3 days at room temperature with food and water ad libitum and ambient illumination on a 12-hour/12-hour light/dark cycle with the light phase consisting of an intensity of approximately 50 lux.

Following the three day period after detachment surgery and PEG administration, the animals are sacrificed and the eyes are enucleated perimortem and immersion fixed for 10 minutes in 4% paraformaldehyde in phosphate-buffered saline (PBS) at pH 7.4. The cornea and lens are removed and the eyecup is divided into segments that span the point of detachment.

The isolated tissue is sectioned on a cryostat or on a Vibratome (Technical Products International, Warrington, Pa.). For cryosections, the segments are washed briefly in PBS and then placed in 15% sucrose until they sink. The pieces are then embedded and cryosectioned at 20 μm. The tissue destined for Vibratome sectioning is not dehydrated. After fixation, this tissue is rinsed in PBS and embedded in 5% agarose in PBS. Sections of 100 μm in thickness are cut with the Vibratome.

To detect dying (apoptotic) cells in situ, the terminal deoxytransferase-mediated dUTP nick end labeling (TUNEL) technique is used to demonstrate the fragmentation of DNA characteristic of apoptosis, following the protocol for cryosections using the fluorescent marker usually Cy3. See Egensperger, et al., Dev. Brain Res. 97:1–8 (1996). To provide general DNA labeling, the Vibratome sections are incubated for 4 hours in propidium iodide (0.5 μg/ml in PBS).

To label cone sheaths by the method of Blanks et al. (Invest. Ophthalmol. Vis. Sci. 25:546–557 (1984)), the cryosections and Vibratome sections are incubated in biotinylated peanut agglutinin (Vector Laboratories, Burlingame, Calif.). The cryosections are incubated for 1 hour in peanut agglutinin diluted in PBS to a final dilution of 400 μg per ml, followed by incubation for 1 hour in streptavidin-Cy1 or Cy3. The Vibratome sections are incubated overnight in the same solutions.

For the immunocytochemical study of the cryosections, incubation times for the blocking serum (10% normal goat serum) and for the primary and secondary antibodies are 1 to 2 hours, and the primary antibody is made up in PBS containing Triton X-100 0.3%. For the Vibratome sections, staining times for the blocking serum (normal donkey serum, 1:20), primary antibody, and secondary antibody are 24 hours for each step to allow adequate penetration into the thick sections. Buffer rinses of 1.5 hours are performed between all antibody steps. All antibodies and rinse solutions are made up in PBS containing bovine serum albumin (0.5%) and Triton-X 100 0.1%. On completion of the staining, the sections are mounted in 5% n-propyl gallate in glycerol. The cryosections and Vibratome sections are labeled with antibodies to cytochrome oxidase (Molecular Probes, Eugene, Oreg.) at 1 μg per ml; antibodies to rod opsin at 1:100; antibodies to blue and red-green cone opsins at 1:100; to synaptophysin at 1:1000; antibodies to glial fibrillary acidic protein 1:500; antibodies to Ki-67 (the MIB-1 antibody of Immunotech, Inc., Westbrook, Mass.) at 1:100; antibodies to β-tubulin at 1:1000; and antibodies to basic fibroblast growth factor (bFGF) (Upstate Biotechnology, Lake Placid, N.Y.) 1:200 (Valter K., Maslim J., Bowers F., Stone J., Photoreceptor dystrophy in the RCS rat: roles of oxygen, debris and bFGF, *Invest Ophthalmol Vis Sci* 1998; 39:2427–2442). The secondary antibodies conjugated to Cy2 or Cy3 (Jackson ImmunoResearch Laboratories, West Grove, Pa.) are diluted 1:200 or 1:1000.

In situ hybridization is performed with cRNA probes prepared from a 477-bp cDNA strand corresponding to nucleotides 533–1009 of a rat ovarian bFGF cDNA. This cDNA incorporates the complete bFGF coding sequence and a 75 nucleotide-3' flanking sequence. The strand is cloned into pBluescript SK$^+$ (Stratagene, San Diego, Calif.) vector. The detailed procedures have been published (Valter K., Maslim J., Bowers F., Stone J., Photoreceptor dystrophy in the RCS rat: roles of oxygen, debris and bFGF, *Invest Ophthalmol Vis Sci* 1998;39:2427–2442).

Observations of the thickness of the outer nuclear layer are made for all the animals after the retinal detachment surgery. Thinning of the outer nuclear layer is observed in those animals that receive PEG-300. Cellular effects of detachment on the neural retina and the retinal pigment epithelium are discussed in: Glaser B M, editor. Retina: surgical retina, Volume 3, St. Louis: C V Mosby, 1989: 165–190). The numbers of animals studied with each technique are as follows: TUNEL for two animals kept in room air and six animals kept in hyperoxia; cone opsin labeling for two and three animals, respectively; peanut agglutinin labeling, two and three animals, respectively; synaptophysin labeling, two and six animals, respectively; cytochrome oxidase labeling, two and five animals, respectively; and bFGF labeling, two and five animals, respectively. Images of retinal tissue are digitized by confocal microscopy. When two fluorophores (red and green) is both digitized, the images are obtained sequentially to maximize signal separation. Wherever signal intensities are to be compared, the photomultiplier tube settings are held constant.

Molecule-specific signals from immunolabeled proteins are quantified by use of NIH Image software (the Analysis tool) from the confocal images. Any optimization of images done before quantitation was kept identical between images to be compared.

Results

Generally, it is found that eyes with detached retinas showed less degeneration as judged by the histochemical analysis described above than eyes with detached retinas that did not receive the PEG composition. More specifically, the detached retinas in the eyes of the cats not treated with PEG (Group II) showed signs of greater retinal degeneration than the eyes of the cats of Group I. These results indicate that the administration of the compositions described herein is effective in limiting retinal damage associated with retinal detachments.

EXAMPLE 7

Reattachment and Damage Protection

A subject presenting a detached retina is administered approximately 100 μl of the formulation of Table 5 once a day for two weeks. The condition of the detached retina is monitored using standard techniques well known in the art. The administration of the PEG-300 formulation promotes retinal reattachment and limits retinal tissue degeneration.

While the present invention has been described in some detail for purposes of clarity and understanding, one skilled in the art will appreciate that various changes in form and detail can be made without departing from the true scope of the invention. All references referred to above are hereby incorporated by reference.

REFERENCES

1. Hageman G S, Marmor M F, Yao X-Y, Johnson L V. The interphotoreceptor matrix mediates primate retinal adhesion. *Arch Ophthalmol.* 1995; 113: 655–60.
2. Marmor M F, Yao X-Y. The metabolic dependency of retinal adhesion in rabbit and primate. *Arch Ophthamol.* 1995; 113: 232–8.
3. Yoon Y H, Marmor M F. Rapid enhancement of retinal adhesion by laser photocoagulation. *Ophthalmology.* 1988; 95: 1385–8.
4. Wilkinson C P, Rice T A. Michels retinal detachment, Ch. 8. Philadelphia: Mosby-Yearbook; 1997: 471–516.
5. Eisner G. Biomicroscopy of the peripheral fundus: an atlas and textbook. New York: Springer-Verlag; 1993: 45.
6. Rosengren B, Osterlin S. Hydrodynamic effects in the vitreous space accompanying eye movements: significance for the pathogenesis of retinal detachment. *Ophthalmologica.* 1976; 173: 513–24.
7. Wilkinson C P, Rice T A. Michel retinal detachment, Ch. 6. Philadelphia: Mosby-Yearbook; 1997: 335–90.
8. Haimann N H, Burton T C, Brown C K. Epidemiology of retinal detachment. *Arch. Ophthalmol.* 1982; 100: 289–92.
9. Goldberg M F. Clear lens extraction for axial myopia. An appraisal. *Ophthalmology.* 1987; 94: 571–82.
10. Javitt J C, Street D A, Tielsch J M, et al. Retinal detachment and endophthalmitis after outpatient cataract surgery. *Ophthalmology.* 1994; 101: 100–6.
11. Duker J S. In: Steinert, ed. Cataract surgery: Technique, complications, and management, Ch. 37. Philadelphia: Saunders; 1995: 434–8.
12. Javitt J C, Tielsch J M, Canner J K, et al. Increased risk of retinal complications associated with Nd: YAG laser capsulotomy. *Ophthalmology.* 1992; 99: 1487–98.
13. Austin K L, Palmer J R, Seddon J M, et al. Case-control study of idiopathic retinal detachment. *Int. J. Epidemiol.* 1990; 19: 1045–50.
14. Wilkinson, C P, Rice T A. Michels retinal detachment, Ch. 4. Philadelphia: Mosby-Yearbook; 1997: 175–250.
15. Brod R D, Flynn H W, Lightran D A. Asymptomatic rhegmatogenous retinal detachments. *Arch. Ophthalmol.* 1995; 113: 1030–1032.
16. Lincoff H, Geiser R. Finding the retinal hole. *Arch. Ophthalmol.* 1971; 85: 565–9.

What is claimed is:

1. A method comprising the steps of:
   administering by ocular route a dose of a glycol ether effective to induce retinal detachment;
   translocating a portion of retinal tissue from a first position to a second position; and reattaching said portion of retinal tissue.

2. The method of claim 1, further comprising the administration of an effective dose of a vitreal humor liquefying agent.

3. A method comprising:
   (a) identifying a patient in need of retinal detachment; and
   (b) administering by ocular route a dose of a glycol ether effective to induce retinal detachment.

4. A method comprising:
   (a) administering by ocular route a dose of a glycol ether effective to induce retinal detachment; and
   (b) measuring retinal detachment.

5. The method of claim 3 or 4, further comprising the administration of an effective dose of a vitreal humor liquefying agent.

6. The method of claim 5, wherein said vitreal humor liquefying agent is selected from the group consisting of glycosaminoglycanases; chondroitin sulfatases; matrix metalloproteinases; and protein-kinases.

7. The method of claim 6, wherein said glycosaminoglycanases are selected from the group consisting of hyaluronidase, hexosaminidase, endo-$\beta$-glucuronidase, keratinase, chondroitinase AC, chondroitinase B and chondroitinase ABC.

8. The method of claim 6, wherein said chondroitin sulfatases are selected from the group consisting of chondroitin 4 sulfatase and chondroitin 6 sulfatase.

9. The method of claim 6, wherein said matrix metalloproteinases are selected from the group consisting of matrix metalloproteinase 1, matrix metalloproteinase 2, matrix metalloproteinase 3 and matrix metalloproteinase 9.

10. The method of claim 6, wherein said protein-kinases are selected from the group consisting of streptokinase and urokinase.

* * * * *